United States Patent [19]
Kantrowitz et al.

[11] Patent Number: 4,809,681
[45] Date of Patent: Mar. 7, 1989

[54] ELECTROCARDIOGRAPHIC MEASUREMENT METHOD FOR CONTROLLING AN INTRA-AORTIC BALLOON PUMP

[75] Inventors: Adrian Kantrowitz, Pontiac; Paul S. Freed, Bloomfield Hills, both of Mich.; Hiroyuki Tachi, Tokyo; Akira Suzuki, Nishio, both of Japan

[73] Assignee: Aisin Seiki Kabushiki Kaisha, Kariya, Japan

[21] Appl. No.: 31,137

[22] Filed: Mar. 30, 1987

Related U.S. Application Data

[62] Division of Ser. No. 845,557, Mar. 28, 1986.

[51] Int. Cl.$^4$ ............................................. A61M 1/00
[52] U.S. Cl. ..................................... 600/17; 128/708
[58] Field of Search ............ 128/1 D, 419 P, 419 PG, 128/642, 695, 696, 697, 708, 710, 784, 788

[56] References Cited

U.S. PATENT DOCUMENTS

| | | | |
|---|---|---|---|
| 3,081,765 | 3/1963 | Kompelien | 128/721 |
| 3,533,403 | 10/1970 | Woodson | 128/642 |
| 3,553,625 | 1/1971 | Stedman | 128/748 |
| 3,585,983 | 6/1971 | Kantrowitz | 128/344 |
| 3,707,960 | 1/1973 | Freed | 128/642 |
| 3,896,803 | 7/1975 | Mason | 604/32 |
| 3,903,897 | 9/1975 | Woollons et al. | 128/642 |
| 3,913,565 | 10/1975 | Kawahara | 128/772 |
| 4,077,394 | 3/1978 | McCurdy | 128/699 |
| 4,148,319 | 4/1979 | Kasper | 604/96 |
| 4,191,193 | 3/1980 | Seo | 128/675 |
| 4,274,423 | 6/1981 | Mizuno et al. | 128/675 |
| 4,284,073 | 8/1981 | Krause et al. | 128/1 D |
| 4,362,150 | 12/1982 | Lombardi, Jr. et al. | |
| 4,552,127 | 11/1985 | Schiff | |
| 4,569,332 | 2/1986 | Schiff et al. | |
| 4,630,597 | 12/1986 | Kantrowitz et al. | 128/1 D |

FOREIGN PATENT DOCUMENTS 995751  2/1983  U.S.S.R. .

OTHER PUBLICATIONS

Mansfield Scientific, Inc. brochure directed to Ventri-Pace Torque and Ventri-Pace Semi-Floater catheters.

*Primary Examiner*—William E. Kamm
*Attorney, Agent, or Firm*—Finnegan, Henderson, Farabow, Garrett & Dunner

[57] ABSTRACT

A pair of spaced electrodes are disposed inside the thoracic aorta near the heart and are used to sense R- and P-waves in an ECG signal. The electrodes are moved to an ideal intra-aortic position, which is that where R- and P-waves are sensed to have the same magnitude, the P-wave, which occurs earlier than the R-wave, serving as means for accurately predicting the occurrence of the R-wave. The electrodes are affixed to the distal end of an intra-aortic balloon, which is capable of being disposed at the ideal position by monitoring of the R- and P-waves sensed by the electrodes. The balloon is deflated at the occurrence of the R-wave, which has been correctly predicted by the earlier P-wave.

2 Claims, 6 Drawing Sheets

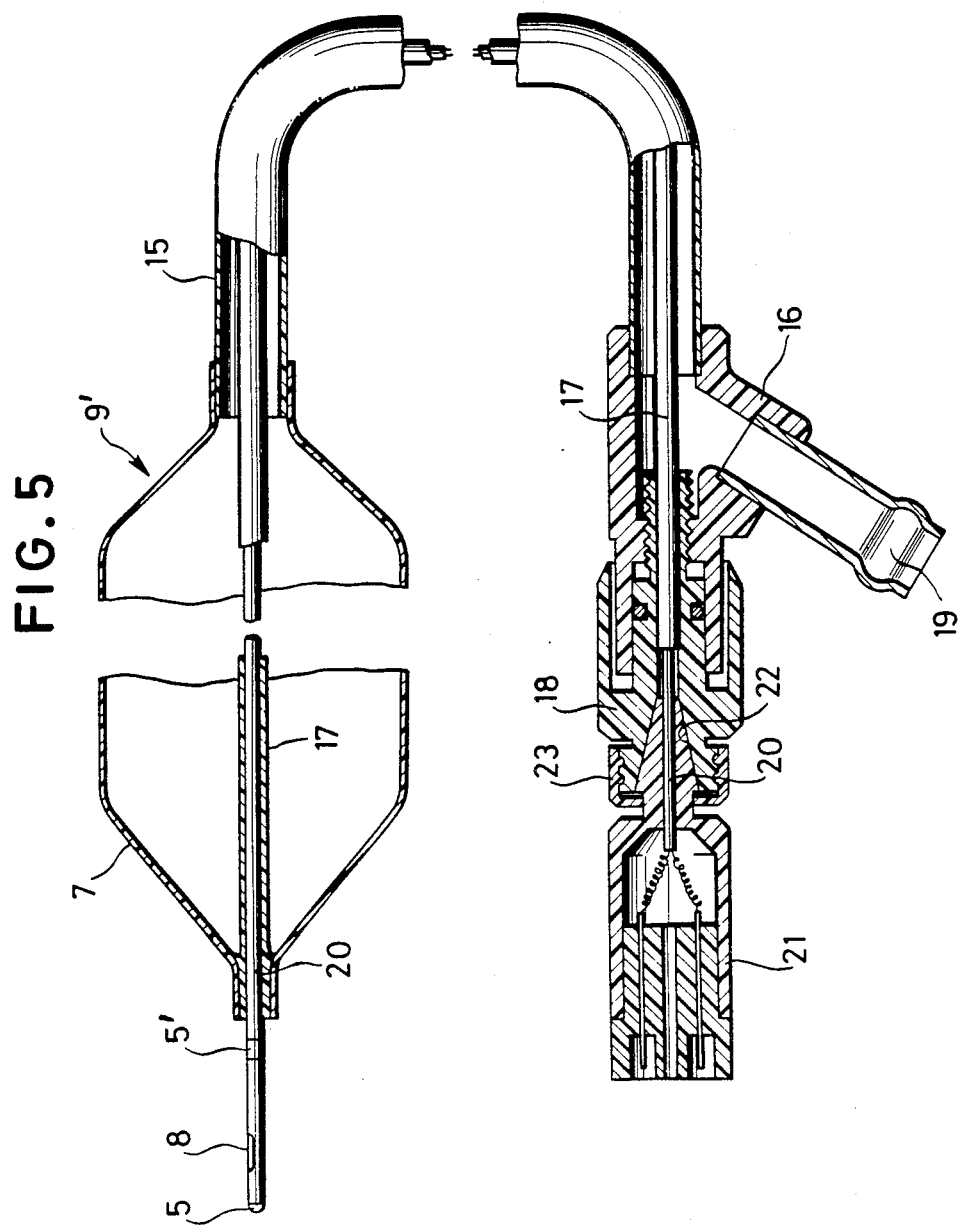

4,809,681

ELECTROCARDIOGRAPHIC MEASUREMENT METHOD FOR CONTROLLING AN INTRA-AORTIC BALLOON PUMP

This is a division of application Ser. No. 845,557, filed Mar. 28, 1986.

BACKGROUND OF THE INVENTION

This invention relates to a method of accurately sensing diastolic and systolic motion of a heart, an intra-aortic balloon apparatus for inflating and deflating a balloon introduced into the aorta in the vicinity of the heart, and a method of disposing the balloon apparatus at the proper intra-aortic position.

It is well-known in the art, as described in, for example, the specification of U.S. Pat. No. 4,362,150, to provide cardiac assistance by introducing a balloon into the thoracic aorta of a patient and causing the balloon to inflate and deflate in accordance with the motion of the patient's heart. A balloon of this type is made to inflate during diastole and deflate during systole. This reduces the load on the left ventricle and raises aortic pressure to increase the blood flow to the coronary and carotid arteries. It is therefore essential that cardiac motion be sensed accurately to enable the balloon to be inflated and deflated correctly in accordance with the cardiac cycle.

Methods of sensing cardiac motion include measurement of aortic pressure and measurement based on an electrocardiographic signal. It has been attempted to combine means for effecting such measurements with the aforementioned intra-aortic balloon apparatus. One example in which an intra-aortic balloon is manipulated while aortic pressure is measured is disclosed in the specification of U.S. Pat. No. 4,077,394, which teaches to inflate the balloon for a prescribed period of time that begins at the occurrence of the dicrotic notch. However, since the disclosed method requires that the aortic blood be withdrawn from the patient through a central tube that passes through the balloon in order that the pressure of the blood may be measured extracorporeally, there is a time delay between actual motion of the patient's heart and a measured value showing the actual motion thereof. Moreover, though the balloon is inflated at the dicrotic notch, the occurrence of the dicrotic notch must first be verified. Owing to the time delay, however, verification of the dicrotic notch lags behinds actual occurrence, with the result that there is a tendency for the balloon to be inflated later than actually required. Additionally, the measured pressure is distorted due to the presence of the long tube, and has motion artifact added to it. both of which made consistent detection of the dicrotic notch difficult. A method of inflating and deflating the balloon based on an ECG signal is set forth in the specification of U.S. Pat. No. 707,960. Here two electrodes are arranged at either end of the balloon, the electrodes sense the ECG signal, and the balloon is inflated and deflated in dependence upon a R-wave contained in the signal. The problem with this method is that in some patients the balloon should be deflated prior to the detection of the R-wave thus necessitating prediction of its occurence.

Other shortcoming common to the prior art include problems in correctly disposing the balloon within the thoracic aorta.

SUMMARY OF THE INVENTION

Accordingly, an object of the present invention is to solve the aforementioned problems encountered in the prior art.

Another object of the present invention is to provide a novel method of accurately sensing P- and R-waves of an ECG signal.

Still another object of the present invention is to provide a method of accurately placing an intra-aortic balloon in an aorta while sensing P- and R-waves of in ECG signal.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

FIG. 5 is a sectional view illustrating another embodiment of an intra-aortic balloon apparatus according to the present invention;

DESCRIPTION OF THE PREFERRED EMBODIMENTS

Before describing the present invention in detail, reference will be made to FIGS. 1, 2 and 3, which are useful in understanding the principle of the invention.

Figure 1:
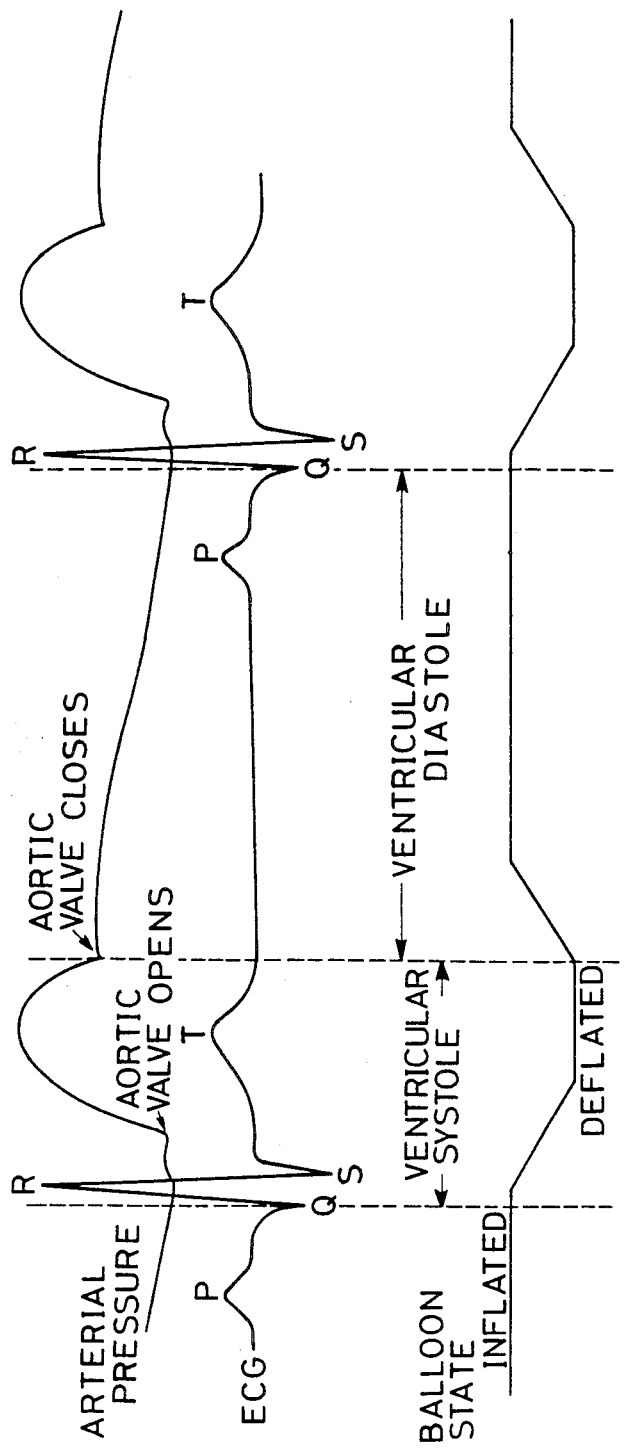
FIG. 1 is a view showing the relationship of aortic blood pressure, ECG and balloon state.

It is evident from FIG. 1, which shows how aortic blood pressure, ECG and balloon state are related, that the R-wave of the ECG occurs after the P-wave. The R-wave gives advance notice of the opening of the aortic valve, and the dicrotic notch appears in the aortic pressure at closure of the aortic valve. Accordingly, the balloon, following its insertion into the aorta, is deflated in response to the R-wave and inflated after the occurrence of the dicrotic notch. It is thus necessary to accurately predict when the R-wave will occur and to deflate the balloon in synchronism with the R-wave. To this end, the inventors have taken note of the significance of the P-wave, which precedes the occurrence of the R-wave, and has considered predicting the occurrence of the R-wave by first accurately sensing the P-wave. However, since the P-wave has but a very small peak in conventional ECG measurement, difficulty is experienced in discriminating between the P-wave and noise. Verification of a distinct P-wave is particularly difficult to achieve in emergency cases where rapid treatment of a patient is required.

Figure 2:
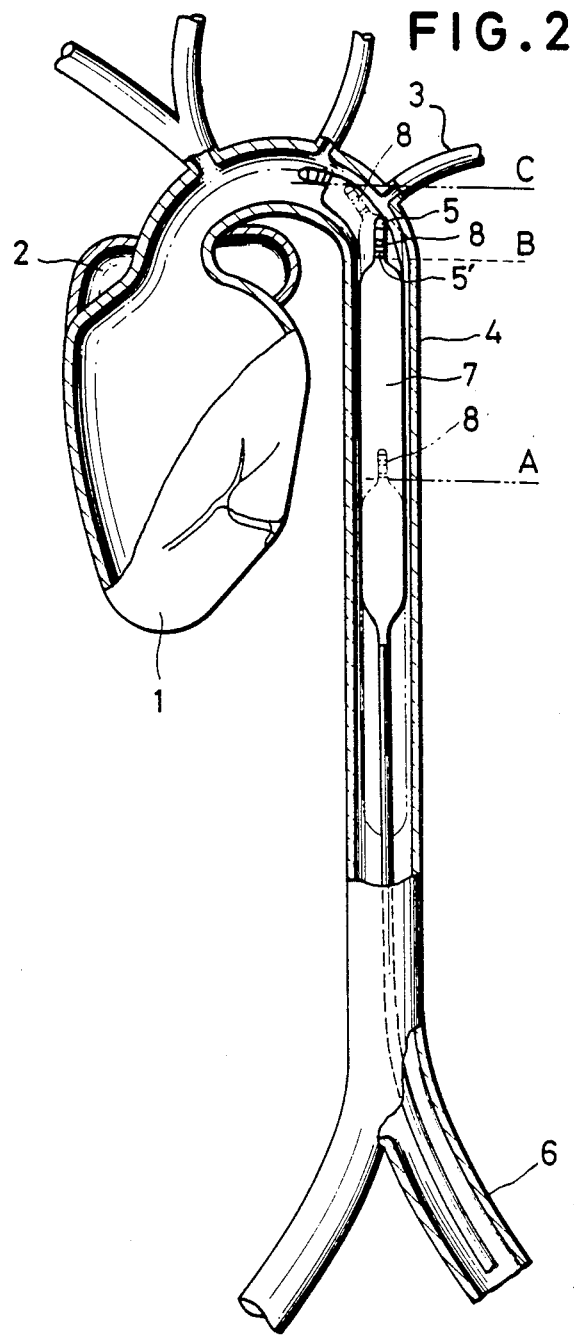
FIG. 2 is a partial sectional view of the vicinity of a human heart and shows electrodes disposed in the patient's aorta.
Figure 3:
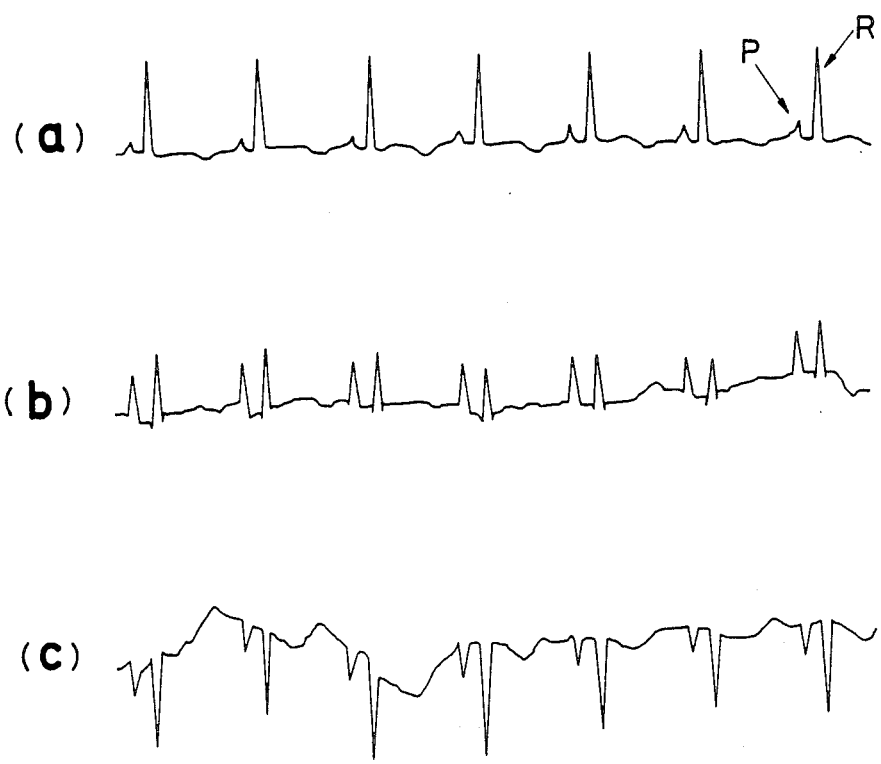
FIG. 3 illustrates three separate waveform diagrams (a), (b), an (c) showing P- and R-waves, the states of which depend upon the position of the electrodes in the aorta.
Figure 7:
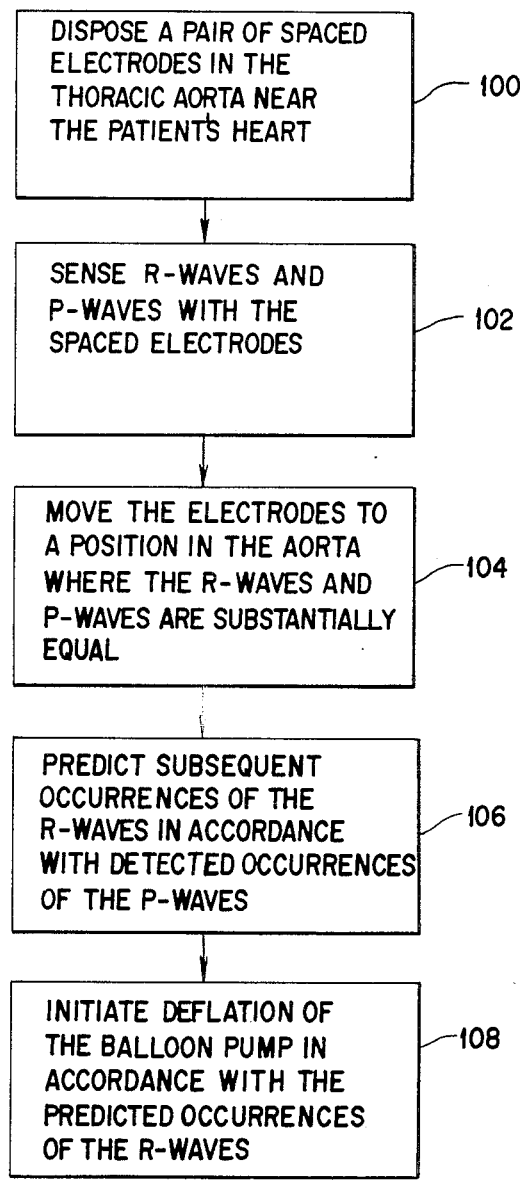
FIG. 7 is a flow chart illustrating the steps of the method of the present invention.

FIG. 2 shows an electrode pair placed in a patient's aorta in the vicinity of the heart. Numeral 1 denotes the ventricle, 2 the atrium, 3 the subclavian arteries, and 4 the aorta. An electrode pair 5' is introduced into the aorta through the femoral artery 6 by percutaneous or surgical means. With the electrodes 5 and 5' located at position A in FIG. 2, a R-wave having a high peak is sensed, but the P-wave is small difficult to verify,. as shown in line (a) of FIG. 3. Moving the electrodes 5 and 5' to the B position in FIG. 2 results in detection of the P- an R-waves as waveforms of substantially the same size, as shown in line (b) of FIG. 3. When the electrodes 5 and 5' are inserted further toward the C position in FIG. 2, first the P- and the R-waves undergo a polarity inversion, as depicted in line (c) of FIG. 3. Therefore, in accordance with the present invention, the electrodes 5, 5' are introduced into the aorta 4, and obtained by them the electrocardiogram is monitored. The electrodes 5, 5' are advanced further into the aorta 4 if the waveform produced is as shown in line (a) of FIG. 3, and are withdrawn an appropriate amount if the waveform obtained is as shown in line (c) of FIG. 3, with the object being to eventually dispose the electrodes 5, 5' and the balloon 7 at an optimum intra-aortic position, namely position B, such that the tip of balloon pump lies within 2 cm of the origin of the left subclavian artery. As a re-sult, the P-wave can be sensed in an accurate fashion, thereby enabling the occurrence of the R-wave to be predicated so that the balloon may be deflated in synchronism the R-wave. The method of the present invention is illustrated in the flowchart of FIG. 7 showing steps 100–108.

A pressure transducer 8 is arranged near the pair of electrodes 5,5' for sensing the aortic blood pressure which enables detection of the dicrotic notch (see FIG. 1), so that the balloon 7 may be inflated in dependence upon the occurrence of the dicrotic notch.

Inflation and deflation of the balloon 7 may be controlled by various computerized means. One example is to feed the P- and R-wave signals into a computer, which would be programmed to control a gas feed mechanism so as to discharge helium gas from the interior of the balloon 7 in synchronism with the R-wave to deflate the balloon, feed helium gas into the balloon 7 after a prescribed period of time to inflate the balloon, and then discharge the gas in response to the next R-wave signal. The computer would repeat these steps in the manner described. Another example is to feed the P- and R-waves and a signal indicative of the dicrotic notch into a computer, which would be programmed to control a gas feed mechanism so as to discharge the gas from the balloon 7 in synchronism with the R-wave and feed gas into the balloon 7 in synchronism with the occurrence of the dicrotic notch.

Figure 4:
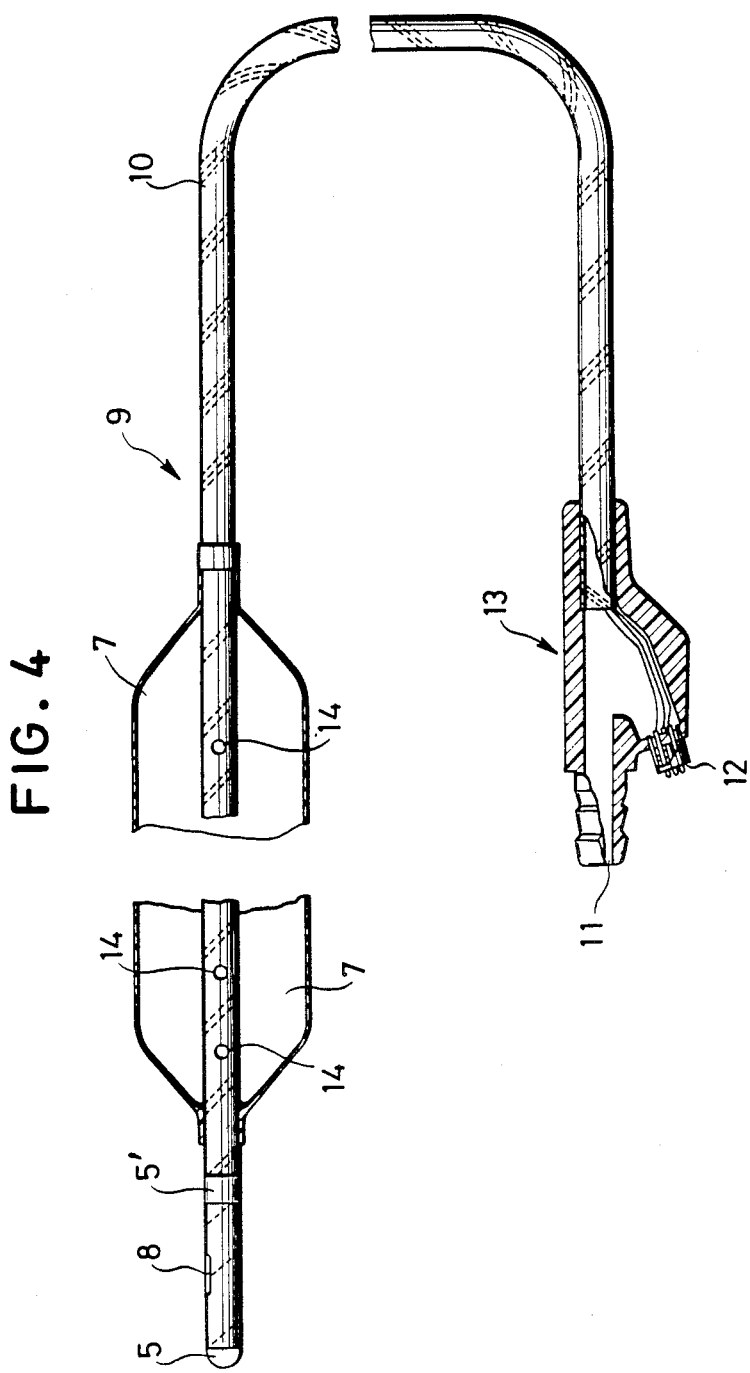
FIG. 4 is a sectional view illustrating an embodiment of an intra-aortic balloon apparatus according to the present invention.

An embodiment of a intra-aortic balloon apparatus practicing the foregoing method of the present invention is indicated generally at numeral 9 in FIG. 4. The balloon 7 is provided with a soft and flexible, slender tube-like catheter 10 that passes through the interior of the balloon 7, the distal end of the catheter 10 extending beyond the distal end of the balloon 7, The catheter 10 has a proximate end to which is secured a coupling 13 having a gas supply port 11 and electric terminals 12. The catheter 10 defines an internal passageway and its wall is perforated with a plurality of small holes 14 at the portion thereof to which the balloon 7 is attached. The gas supply port 11 and the interior of the balloon are thus communicating via the small holes 14 and the passageway inside the catheter 10. The balloon 7 is inflated and deflated by controlling the inflow and outflow of gas to and from the gas supply port 11.

The electrode pair 5,5' disposed are at the distal end of the catheter 10 protruding from the distal end of balloon 7. The pressure transducer 8 is disposed between the electrodes 5,5' which are spaced apart by about 2 cm. Lead wires connected at their one ends to the electrodes 5', 5'' and to the pressure transducer 8 are wound in helical form along the inner wall surface of the catheter 10 and extend into the coupling 13 where they are connected at their other ends to the terminals 12.

The intra-aortic balloon apparatus 9 having the foregoing construction is inserted into the aorta through the femoral artery by surgical introduction and senses the P- and R-waves via the electrodes 5, 5' or 5''. The apparatus is disposed at an intra-aortic position at which the sensed P- and R-waves will be of approximately the same magnitude, as described earlier. withdrawal of the gas from the balloon 7 is synchronized to the R-wave signal from the electrodes 5, 5' and feed of gas to the balloon 7 is synchronized with the dicrotic notch signal from the pressure transducer 8.

Another embodiment of an intra-aortic balloon apparatus according to the present invention will now be described with reference to FIG. 5. The apparatus, shown generally at numeral 9', includes a tubular first catheter 15 having a proximate end joined to a Y-shaped connector 16 and a distal end supporting a proximate end of the balloon 7 air-tightly. A central tubular member 17 extends through the interior of the first catheter 15 and has a distal end of comparatively larger diameter projecting from the distal end of first catheter 15 and air-tightly supporting the distal end of the balloon 7. The central tubular member 17 has a proximate end fixedly secured to a rotary member 18 baving a portion in threaded engagement with the connector 16. Turning the rotary member 18 with respect to the connector 16 rotates the tubular member 17 so that the balloon 7 may be wrapped around the tubular member 17 by rotating the same in one direction and unwrapped from the tubular member 17 by rotating same in the opposite direction. The connector 16 has a port 19 from which a fluid such as helium gas is introduced from an external source, not shown. The gas is fed from connector 16 into the balloon 7 through a passageway defined between the inner surface of first catheter 15 and the outer surface of tubular member 17, whereby the balloon 7 is made to inflate. Withdrawing the gas from the balloon through the same passageway causes the balloon to deflate.

A tubular second catheter 20, the diameter whereof is smaller than that of the first catheter 15, is capable of being passed through the passageway of the central tubular member 17 and has a distal end that projects from the distal end of the tubular member 17. The second catheter 20 has a proximate end secured to a second connector 21. The second connector 21 has a tapered distal end portion 22 lockably fitted into a tapered bore formed inside the rotary member 18. A knob 23 is provided for releasably locking the second connector 21 to the rotary member 18.

The electrode pair 5, 5' and pressure transducer 8 are disposed at the distal end portIon of the second catheter 20. The lead wires from the electrodes 5, 5' and transducer 8 are wound in helical fashion along inner wall surface of the second catheter 20 and are connected to terminals in the second connector 21. The second connector 21 is in turn connected to arithmetic circuitry, not shown, the function whereof is described hereinbelow.

To use the intra-aortic balloon apparatus 9' shown in FIG. 5, a guide wire, not shown, is inserted into the aorta from the patient's femoral region as by the Seldinger method and is passed along the aorta until the leading end of the guide wire reaches the vicinity of the patient's heart. Next, the other end of the guide wire is inserted into the passageway of tubular member 17, into which the second catheter 20 has not yet been introduced. The tubular member 17, with the balloon 7 wrapped around it, is then introduced together with the first catheter 15 into the aorta while being guided along the guide wire. When these have reached a predetermined position inside the aorta, the guide wire is withdrawn from the patient's body through the passageway in tubular member 17. This is followed by inserting the distal end of the second catheter 20 into the tubular member 17 and then introducing the distal end of the second catheter 20 into the aorta through the tubular member 17 while manipulating the connector 21 to which the second catheter 20 is affixed. The tapered distal end portion 22 of second connector 21 is brought into abutting contact with the rotary member 18 and the knob 23 is turned to lock the second connector 21 and rotary member 18 together. The connector 21 is connected to the aforementioned arithmetic circuit, not shown, and the electrodes 5, 5' at the distal end of the second catheter 20 sense the P- and R-waves. The resulting signals are monitored so that the balloon 7 may be moved to the correct intra-aortic position by manipulating the connector 21. Thus, the balloon 7 has thus been moved to the correct position.

The aforementioned arithmetic circuit receives the P- and R-wave signals from the electrodes 5, 5' and the aortic pressure signal from the pressure transducer 8 to calculate the counterpulsation timing in accordance with these signals. The balloon 7 is caused to inflate and deflate at the timing calculated.

Figure 6:
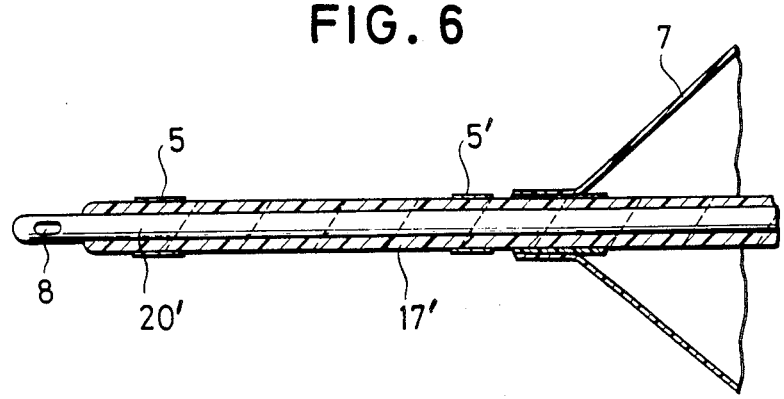
FIG. 6 is a partial sectional view illustrating a third embodiment of an intra-aortic balloon apparatus according to the present invention.

In an embodiment of the intra-aortic balloon apparatus shown in FIG. 6, the distal end of the tubular member, indicated at numeral 17', is extended beyond the distal end of balloon 7, and the electrodes 5, 5' are disposed on the extended portion of the tubular member 17'. The pressure transducer 8, on the other hand, is attached to the distal end of the second catheter, here shown at numeral 20'. With this arrangement, the second catheter 20' need not be used if measurement of aortic blood pressure is unnecessary. In such case, the electrodes 5 sense the P- and R-waves and the balloon 7 is disposed at the correct intra-aortic position, deflated in response to the R-wave and inflated upon passage of a prescribed period of time. Note that the lead wires from the electrodes 5, 5' are imbedded in the wall of the tubular member 17' and may be connected to the Y-shaped first connector 16 (FIG. 5) so that the signals from the electrodes 5, 5' may be extracted from the connector 16. When the second catheter 20' is not used, a plug (not shown) is fitted into the rotary member 18 in place of the connector 21.

It will be evident from the foregoing description that the present invention makes it possible for the balloon to be inflated and deflated in correct response to the actions of the patient's heart, and that the invention enables the balloon-to be disposed at the proper intra-aortic position with greater precision.

As many apparently widely different embodiments of the present invention can be made without departing from the spirit and scope thereof, it is to be understood that the invention is not limited to the specific embodiments thereof except as definded in the appended claims.

What is claimed is:

1. An electrocardiographic measurement method for assistance in controlling deflation of an intra-aortic balloon pump disposed in the thoracic aorta of a patient, comprising the steps of:

disposing at least a pair of spaced electrodes inside the thoracic aorta near the patient's heart;

sensing R-waves and P-waves by said electrodes;

moving said electrodes to a position in the thoracic aorta where the R- and P-waves are substantially equal in magnitude for accurately detecting the occurrence of the P-wave;

predicting subsequent occurrences of the R-waves in accordance with the detected occurrences of the P-waves; and initiating deflation of the intra-aortic balloon pump in accordance with the predicted subsequent occurrences of the R-waves such that the balloon pump is deflated synchronously with each R-wave occurrence.

2. The electrocardiographic method according to claim 1, wherein the step of moving said electrodes include the substeps of:

inserting the electrodes into a deeper region in the thoracic aorta when the R-wave is larger than the P-wave at a first present position in the thoracic aorta;

withdrawing the electrodes into a shallower region in the thoracic aorta when the R-wave and P-wave change polarity at a second present position in the thoracic aorta; and determining a position intermediate said first and second present positions in the thoracic aorta at which the R- and P-waves are substantially equal in magnitude.

* * * * *